United States Patent
Bender et al.

(10) Patent No.: US 10,977,921 B2
(45) Date of Patent: Apr. 13, 2021

(54) COGNITIVE ANALYSIS OF BIOSENSOR DATA

(71) Applicant: INTERNATIONAL BUSINESS MACHINES CORPORATION, Armonk, NY (US)

(72) Inventors: Michael Bender, Rye Brook, NY (US); Rhonda L. Childress, Austin, TX (US); Andrew Barnes, Greystones (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/201,199

(22) Filed: Nov. 27, 2018

(65) Prior Publication Data

US 2020/0168070 A1 May 28, 2020

(51) Int. Cl.
*G08B 21/04* (2006.01)
*G06F 1/16* (2006.01)
*G16H 50/30* (2018.01)

(52) U.S. Cl.
CPC ......... *G08B 21/0453* (2013.01); *G06F 1/163* (2013.01); *G16H 50/30* (2018.01)

(58) Field of Classification Search
CPC .................................... H04L 1/00; G06F 1/00
See application file for complete search history.

(56) References Cited

U.S. PATENT DOCUMENTS

| | | | |
|---|---|---|---|
| 9,940,846 B2 | 4/2018 | Mayou et al. | |
| 2015/0120317 A1* | 4/2015 | Mayou ................... | G09B 19/00 705/2 |
| 2017/0344854 A1* | 11/2017 | Behringer .............. | G06N 20/00 |
| 2018/0151055 A1 | 5/2018 | Prokofyeva et al. | |
| 2018/0153012 A1 | 5/2018 | Lee et al. | |
| 2018/0357887 A1* | 12/2018 | Geyer .................. | G08B 25/016 |
| 2019/0095793 A1* | 3/2019 | Fink .................... | A61B 5/02438 |
| 2019/0328300 A1* | 10/2019 | Bozorgtabar ......... | A61B 5/1114 |
| 2019/0328307 A1* | 10/2019 | Osorio ................ | A61B 5/0205 |

FOREIGN PATENT DOCUMENTS

KR      101859399 B1    5/2018

* cited by examiner

*Primary Examiner* — Shirley Lu
(74) *Attorney, Agent, or Firm* — Tutunjian & Bitetto, P.C.; Michael A. Petrocelli

(57) ABSTRACT

A method and system for issuing medical alerts that includes receiving permission from a user to register the user with a medical alert system. With permission from the user, registering includes setting a medical history for a baseline of the user, and linking the system with a wearable device including a light source for signaling changes in the users medical condition. The method also includes linking a monitoring device to the medical alert system; and measuring changes in the health status of the user with the monitoring device. In some embodiments, the method further includes determining with a cognitive risk evaluating engine of the medical alert system a level of medical alert provided by a setting of the light source that corresponds the users health. The method can further include illuminating the light source at the level of the medical alert designed by the cognitive risk evaluating engine for signaling the changes in the users medical condition.

13 Claims, 7 Drawing Sheets

COGNITIVE ANALYSIS OF BIOSENSOR DATA

BACKGROUND

Technical Field

The present invention generally relates to medical alerts, and more particularly to wearable medical alert devices.

Description of the Related Art

People with medical conditions that have secondary intervention currently have devices with alarms that may sound to trigger the attention. However, they do not always want the alarm to be noticed by everyone. This is especially important to children and teens, for example where Type 1 diabetes needs to be carefully monitored. Such discrete, smart, notification mechanisms can significantly improve quality of life, and also assist a care-giver managing multiple people, an ability to visually triage those in their care.

SUMMARY

In accordance with an embodiment of the present disclosure, a method is provided for issuing medical alerts that employs a wearable decorative device that illuminates a light source of the device to signal the health status of a user that is wearing the wearable decorative device. In one embodiment, the method includes registering a user with a medical alert system. Registering can include setting a medical history for a baseline of the user, and linking the system with a wearable device including a light source for signaling changes in the users medical condition from a baseline of the user. The method may further include linking a monitoring device to the medical alert system; and measuring changes in a health status of a user from the baseline of the user using the monitoring device. The method can continue with determining with a cognitive risk evaluating engine of the medical alert system a level of medical alert provided by a setting of the light source that corresponds to the changes in the users health status measured by the monitoring device. In a following step, the method includes illuminating the light source at the level of the medical alert designed by the cognitive risk evaluating engine for signaling the changes in the users medical condition from the baseline of the user.

In another aspect of the present disclosure, a system is provided for issuing medical alerts. In one embodiment, the alert system includes a wearable device including a light source for signaling medical alerts. The system may further include registry linking the wearable device to a user medical history, wherein the medical history provides a baseline of the user. A monitoring device receiver for receiving from a monitoring device measurements of changes in a health status of a user from the baseline of the user. The system also includes a cognitive risk evaluating engine for setting a level of medical alert that is to be provided by the light source. The level of medical alert provided by the light source corresponds to the severity of the changes in the users health status that is measured by the monitoring device. The system may further include a transmitter for sending a signal to illuminate the light source at the level of the medical alert designated by the cognitive risk evaluating engine.

In another aspect, a computer program product is provided that provides for issuing medical alerts. In one embodiment, the computer program product includes a non-transitory computer readable storage medium having computer readable program code embodied therein for issuing medical alerts. The method stored on the computer readable storage medium can include registering a user with a medical alert system. Registering can include setting a medical history for a baseline of the user, and linking the system with a wearable device including a light source for signaling changes in the users medical condition from a baseline of the user. The method may further include linking a monitoring device to the medical alert system; and measuring changes in a health status of a user from the baseline of the user using the monitoring device. The method can continue with determining with a cognitive risk evaluating engine of the medical alert system a level of medical alert provided by a setting of the light source that corresponds to the changes in the users health status measured by the monitoring device. In a following step, the method includes illuminating the light source at the level of the medical alert designed by the cognitive risk evaluating engine for signaling the changes in the users medical condition from the baseline of the user.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

In some embodiments, the disclosure provides methods, systems and computer program products provide a medical alert system. People with medical conditions that may require secondary intervention currently have devices with alarms that may sound to trigger the attention. However, they do not always want the alarm to be noticed by everyone. This is especially important to children and teens, e.g., where Type 1 diabetes needs to be carefully monitored. Such discrete, notification mechanisms can improve quality of life, and also assist a care-giver managing multiple people, an ability to visually triage those in their care.

The methods, systems and computer program products that are described herein provide a user interface that incorporates a lighting source, such as LED lighting (or other form of illumination), into wearable decorative alert device, which can have a jewelry like form factor, such as a necklace, ring, earing, bracelet, and combinations thereof. Incorporating a light source that can be illuminated to signal a medical alert into the jewelry of a user can make that jewelry into an Internet of things (TOT) device. The Internet of things (IoT) is the network of physical devices, vehicles, home appliances, and other items embedded with electronics, software, sensors, actuators, and connectivity which enables these things to connect, collect and exchange data. In some embodiments, depending on the urgency of a user's medical condition, different levels and types of lighting, such as different light patterns, will be initiated to signal different urgency of the user's medical condition. In some embodiments, the methods, systems and computer program product's of the present disclosure can link a cognitive back-end engine that will learn the different levels of urgency that are needed, based on an individual's history. The urgency is also determined by utilizing other IoT devices, such as devices having video and/or audio recording abilities, to determine change of state of an individual's physical capabilities which can be important if a care-giver needs to attend to multiple individuals at the same time. The systems, methods and computer program products are now described with more detail with reference to FIGS. 1-7.

Figure 1:
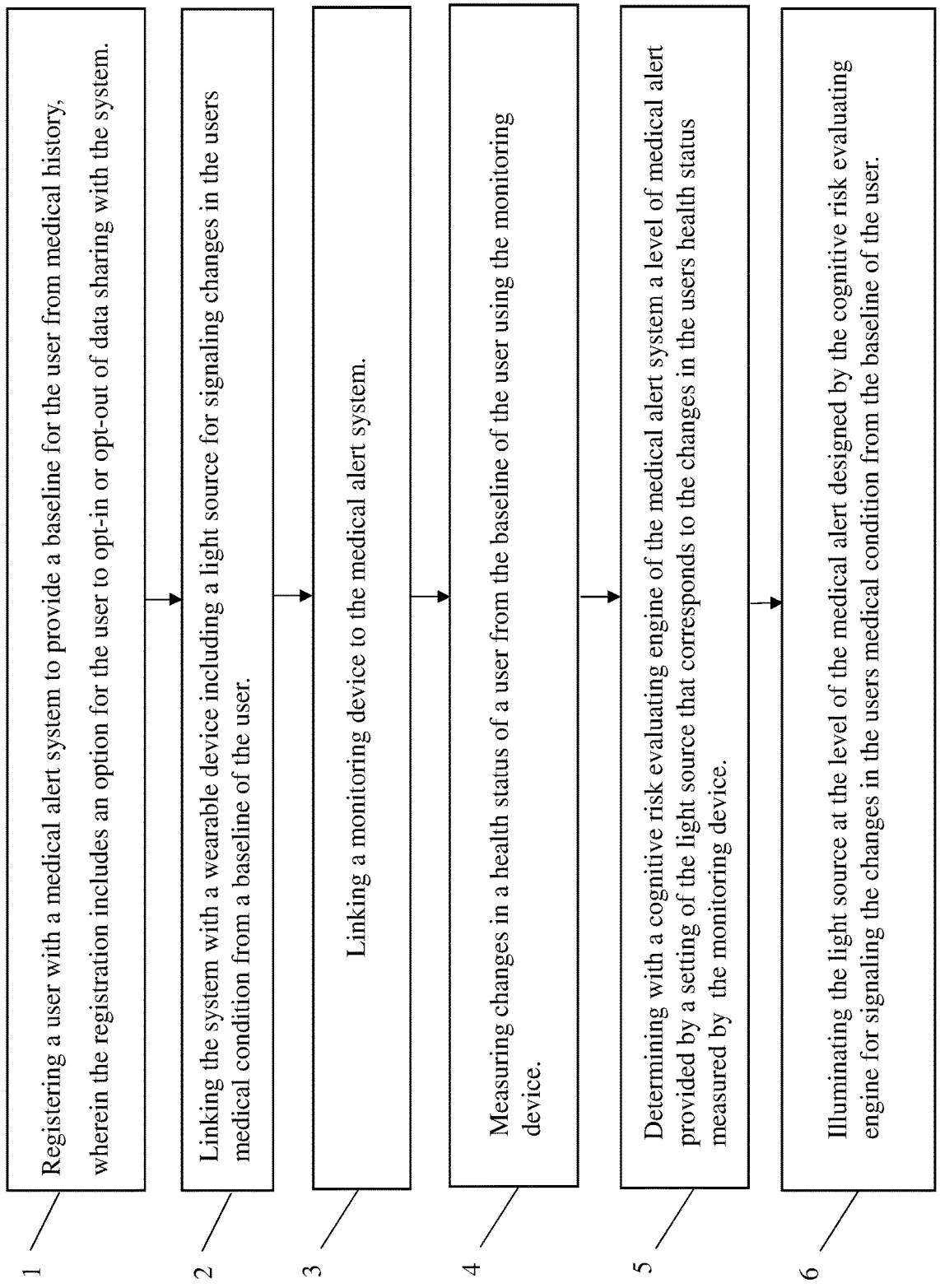
FIG. 1 is a block/flow diagram showing a method of providing medical alert by incorporating a light source into a wearable decorative alert device, in accordance with an embodiment of the present invention.

FIG. 1 is a block/flow diagram showing a method of providing medical alert by incorporating a light source into a wearable decorative alert device 10. The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
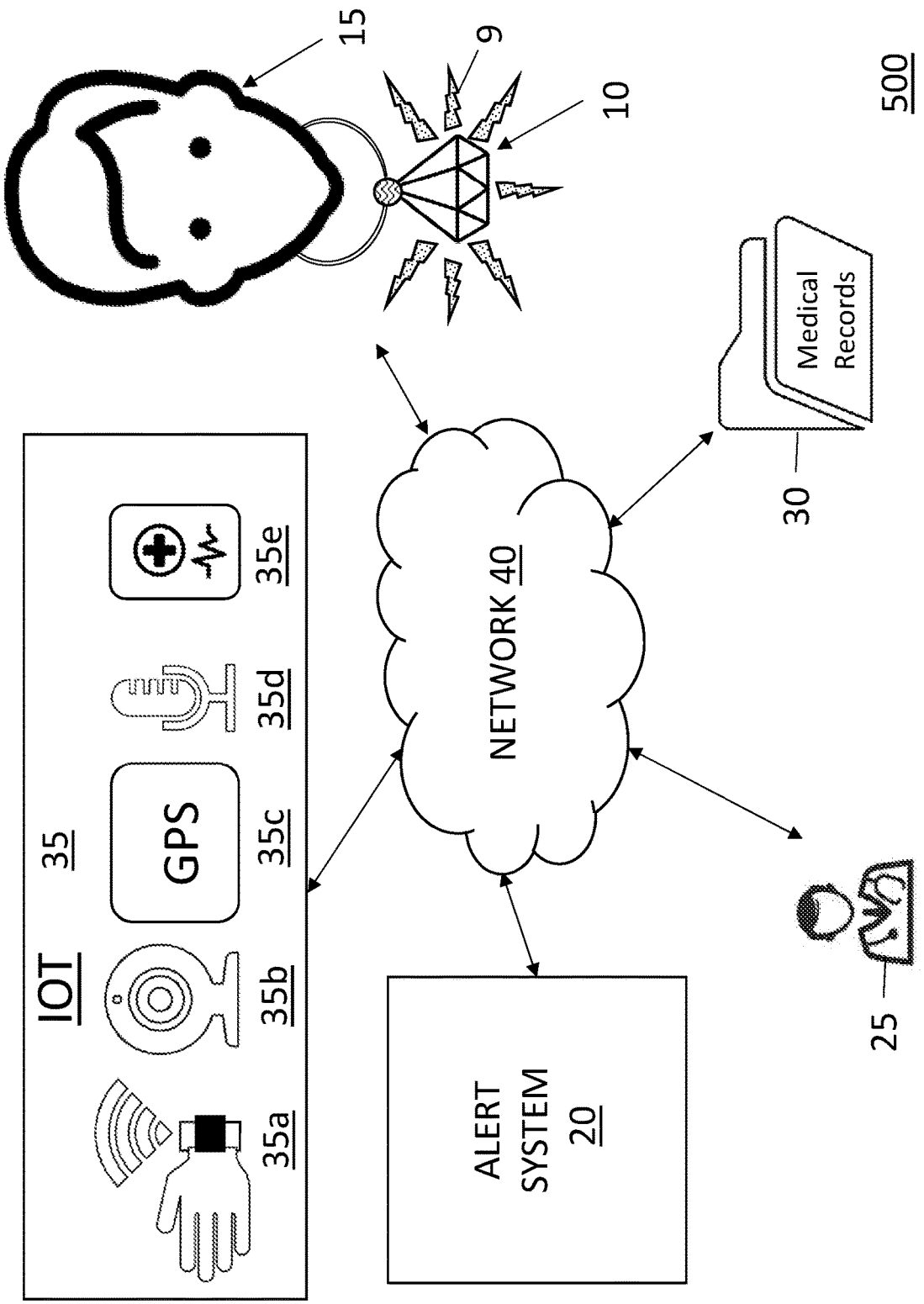
FIG. 2 is a diagram illustrating an example environment for providing a medical alert by incorporating a light source into a wearable decorative alert device, in accordance with one embodiment of the present disclosure.

In some embodiments, the method may begin at block 1, which can include registering a user with a medical alert system 20 to provide a baseline 15 for the user from medical history, e.g., medical records. FIG. 2 is a diagram illustrating an example environment for providing a medical alert by incorporating a light source into a wearable decorative alert device 10.

Registration means that addresses for users 15 are provided to the medical alert system 20 and recorded in a form of memory, e.g., hardware memory, so that all the devices needed for the medical alert system 20 to collect and analyze health status data of a user 15, as well as addresses for the medical alert system 20 to send medical alert signals to be displayed on the wearable decorative alert device 10 of the user 15, are associated to that specific user 15 to provide for interconnection over a network 40.

Registration includes an option for the user 15 to opt-in or opt-out of data sharing with the system. To the extent implementations of the invention collect, store, or employ personal information provided by, or obtained from, individuals (for example, current locations of drivers, historical records of drivers, etc.), such information shall be used in accordance with all applicable laws concerning protection of personal information. Additionally, the collection, storage, and use of such information may be subject to consent of the individual, i.e., user 15, to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information. The user may also revoke his opt in status at any time.

One or more portions of the network 40 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, a wireless network, a WiFi network, a WiMax network, another type of network, or a combination of two or more such networks. Any one or more portions of the network 40 may communicate information via a transmission medium. As used herein, "transmission medium" refers to any intangible (e.g., transitory) medium that is capable of communicating (e.g., transmitting) instructions for execution by a machine (e.g., by one or more processors of such a machine), and includes digital or analog communication signals or other intangible media to facilitate communication of such software.

With the user's permission via registration, the medical alert system 20 can be linked to a user's medical history, e.g., linking over the network 40 to a database of medical records 30 corresponding to the user 15. The medical history in clinical medicine is the patient's past and present, which may contain relevant information bearing on their health past, present, and future. The medical history is an account of all medical events and problems a person has experienced is an important tool in the management of the patient.

Registration may include linking the medical alert system 20 to a user's medical care professional 25. A medical care professional 25 may be a health professional may operate within all branches of health care, including medicine, surgery, dentistry, midwifery, pharmacy, psychology, nursing or allied health professions. The medical care professional 25 can be selected from the group consisting of physicians, dentists, pharmacists, pharmacy technicians, physician assistants, nurses, advanced practice registered nurses, surgeons, surgeon's assistant, exercise physiologists, surgical technologist, dietitians, nutritionists, therapists, chiropractors, physical therapists, respiratory therapists, emergency medical technicians, paramedics, medical laboratory scientists, medical prosthetic technicians and combinations thereof.

The medical care professional 25 and the database of medical records 30 registered with the medial alert system 20 allows for the baseline for the user's health to be entered into the system. The baseline for the user's health can include information on the malady, e.g., disease or ailment, for which the user is wearing the wearable decorative alert device 10. The malady can be any illness, sickness, disease, infection, ailment, disorder, complaint, indisposition, affliction, infirmity, syndrome for which the user 15 may include treatment. In one example, the malady can be diabetes. In another example, the malady can be heart disease.

In some embodiments, setting the baseline includes setting a criteria at which one met by a measurement of the users conduct or a particular qualitative health indicator of health status for triggering a medical alert. For example, if the malady being treated was heart disease, a qualitative health indicator that could be used as the threshold for issuing a health alert could be a measurement of a user' heartbeat outside of a healthy range. The suitable heartbeat rates, and unsuitable heartbeat rates, could be set by the medical care professional 25 in combination with the database of medical records 30. In another example, if the malady being treated was heart disease, health indicators measured from the users conduct that could be used as the threshold for issuing a health alert could be a measurement, e.g., by visual recording, and/or audio recording and/or health diagnostic measurement, of chest pain, chest tightness, chest pressure and chest discomfort (angina, shortness of breath, racing heartbeat (tachycardia), slow heartbeat (bradycardia), lightheadedness, dizziness, fainting (syncope) or near fainting. In a further example, if the malady being treated is diabetes, a qualitative health indicator that could be used as the threshold for issuing a health alert could be a measurement of a user's blood sugar levels outside of a healthy range. In yet a further example, if the malady being treated is diabetes, health indicators measured from the users conduct that could be used as the threshold for issuing a health alert could be a measurement, e.g., by visual recording, and/or audio recording and/or health diagnostic measurement, of slurred speech and/or slow motion and/or erratic motion. It is noted that the above examples are provided for illustrative purposes only, and are not intended to limit the present disclosure. For example, in other embodiments, the baseline of the user 25 is a medical characteristic of the user selected from the group consisting of heart rate, blood sugar level, temperature, oxygen level, and combinations thereof. The health baseline may be specifically set for the user account by the medical care professional 25.

Figure 3:
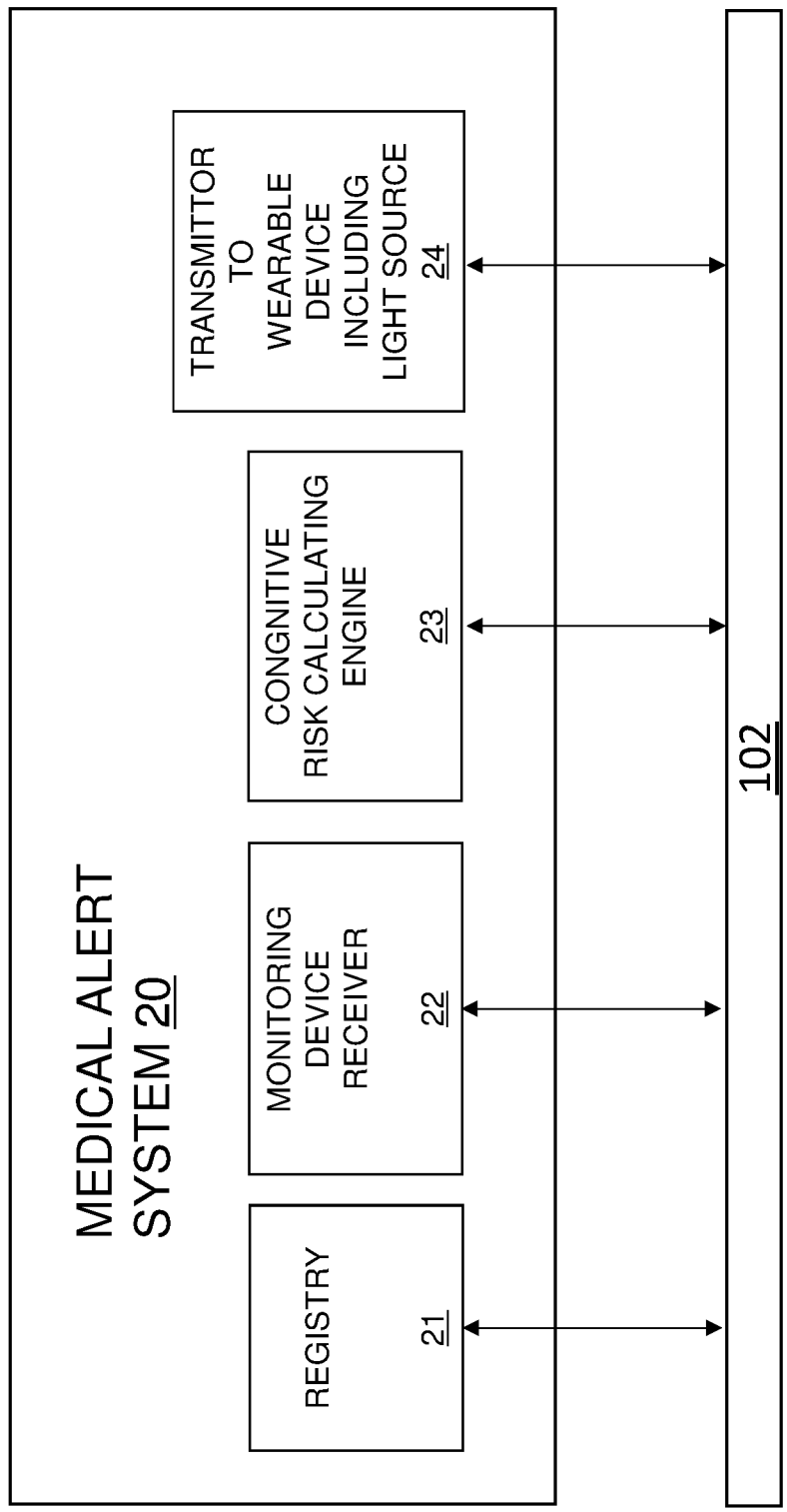
FIG. 3 is a block diagram illustrating a medical alert system that incorporates an activatable light source into a wearable decorative alert device, in which activation of the light source signals a change in the medical status of the wearable decorative alert device, in accordance with one embodiment of the present disclosure.

FIG. 3 illustrates one embodiment of a medical alert system 20 that incorporates an activatable light source into a wearable decorative alert device 10, in which activation of the light source signals a change in the medical status of the wearable decorative alert device. The registry 21 of the medical alert system 20 may be a form of memory, e.g., hardware memory, that stores all the registry information that has been discussed above with reference to block 1 of FIG. 1.

To the extent implementations of the invention collect, store, or employ personal information provided by, or obtained from, individuals (for example, current locations of drivers, historical records of drivers, etc.), such information shall be used in accordance with all applicable laws concerning protection of personal information. Additionally, the collection, storage, and use of such information may be subject to consent of the individual, i.e., user 15, to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

Referring to FIG. 1, at block 2, the method may continue with linking the alert system with a wearable device 10 including a light source 16 for signaling changes, e.g., light 9 signal changes, in the users 15 medical condition from a baseline of the user 15. In some embodiments, the wearable device 10 has a jewelry form factor selected from the group consisting of a ring, a necklace, a wrist band, an ankle band, a head band, earrings or a combination thereof.

Figure 4:
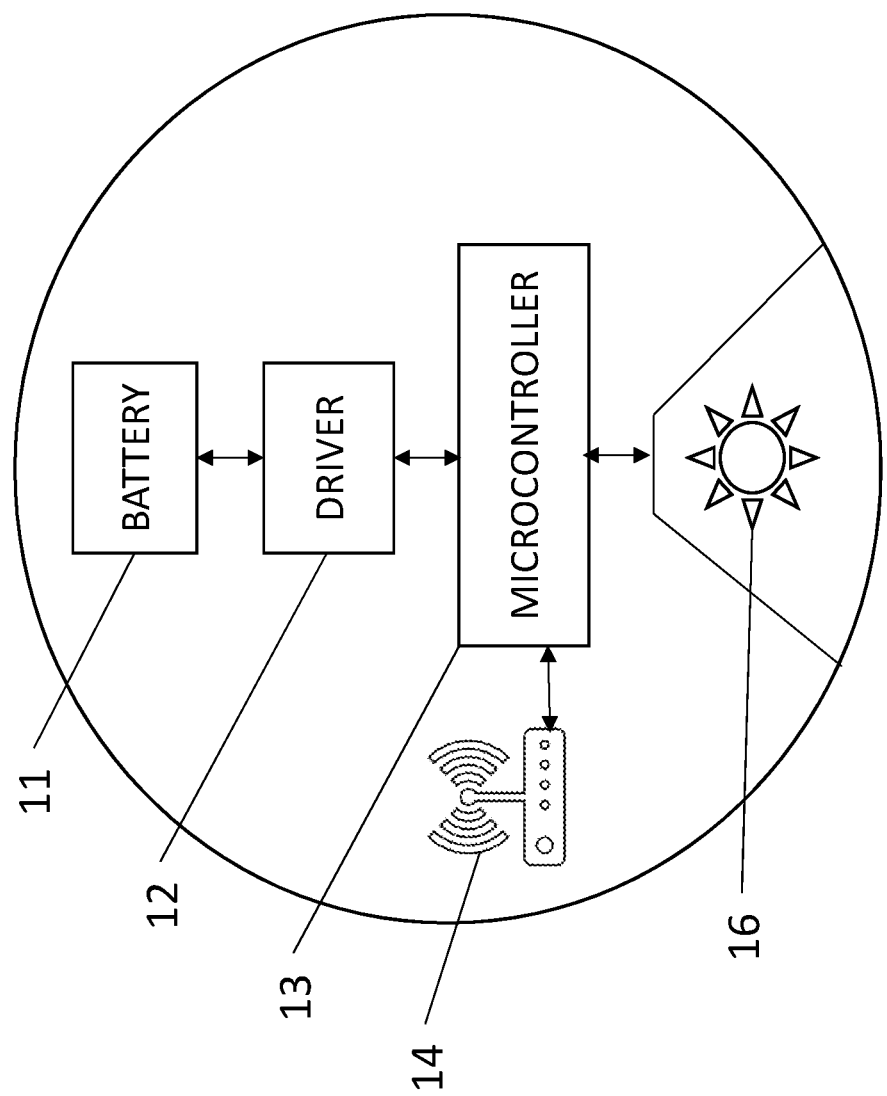
FIG. 4 is a block diagram of a decorative wearable device incorporating a light source to signal medical alerts.

FIG. 4 is a block diagram of a decorative wearable device 10 incorporating a light source 16 to signal medical alerts.

Referring to FIGS. 3 and 4, the wearable decorative alert device 10 is linked to the medical alert system 20. For example, the wearable decorative alert device 10 can include a transceiver 14, as depicted in FIG. 4, and the medical alert system 20 can include a transmitter 24 (e.g., transmitter to wearable device including light source 10) to provide interconnectivity between the wearable decorative alert device 10 and the medical alert system 20. The connection between the wearable decorative alert device 10 and the medical alert system 20 can include cellular radio to establish a connection to the Internet via a cellular service such as a 4G (e.g., Mobile WiMAX, LTE) or 5G cellular data service to access the network 40. In one embodiment, the wearable decorative alert device 10 may include a WiFi radio to establish a WiFi connection through a WiFi access point or router which couples the wearable decorative alert device 10 to the Internet (e.g., via an Internet Service Provider providing Internet service to the end user), which in turn connect to the medical alert system 20/network 40. Of course, it should be noted that the underlying principles of the invention are not limited to any particular type of communication channel or protocol. For example, in one embodiment, the wearable decorative alert device 10 may be equipped with Bluetooth LE radios and protocol stacks.

Referring to FIGS. 1, 2 and 4, in some embodiments, the light source 16 of the wearable device 10 includes a form of solid state lighting. The term "solid state" refers to light emitted by solid-state electroluminescence, as opposed to incandescent bulbs (which use thermal radiation) or fluorescent tubes, which use a low-pressure Hg discharge. In a broad sense, a light emitting diode (LED) is a semiconductor device that emits visible light when an electric current passes through it. Some examples of solid state light emitters that are suitable for the methods and structures described herein include inorganic semiconductor light-emitting diodes (LEDs), organic light-emitting diodes (OLED), polymer light-emitting diodes (PLED) or combinations thereof.

The light source 16 of the wearable device 10 is adjustable to provide different colors, color temperatures, and/or intensity of light, or patterns of light, in which these different characteristics of light can be used to signal different types of medical alerts. For example, different colors and/or intensities may be used to signal different types of medical alerts.

In some embodiments, the different colors may be used to signal different severities of medical alerts. The term "color" denotes a phenomenon of light or visual perception that can enable one to differentiate objects. Color may describe an aspect of the appearance of objects and light sources in terms of hue, brightness, and saturation. Some examples of colors that may be suitable for use with the method of controlling lighting in accordance with the methods, systems and computer program products described herein can include red, orange, yellow, green, blue, indigo, violet and combinations thereof, as well as the numerous shades of the aforementioned families of colors. In one example, when the severity of the medical alert being signaled by the wearable device 10 is high, the color may be selected to be red, and when the severity of the medical alert being signaled by the wearable device 10 is low, the color is selected to be yellow.

In some embodiments, different color temperatures may be used to signal different severities of medical alerts. Color temperature is a measurement having the units degrees Kelvin (° K). In some examples, the range of Kelvin selected for the color temperature can range from 1K to 7K. In one example, when the severity of the medical alert being signaled by the wearable device 10 is high, the color temperature may be selected to be low, e.g., 1000K, and when the severity of the medical alert being signaled by the wearable device 10 is low, the color is selected to be high, e.g., 7000K.

In some embodiments, different color intensity may be used to signal different severities of medical alerts. In one example, when the severity of the medical alert being signaled by the wearable device 10 is high, the color intensity may be selected to be high, e.g., bright; and when the severity of the medical alert being signaled by the wearable device 10 is low, the color intensity is to be low, e.g., dim.

Referring to FIG. 4, the wearable decorative alert device 10 may also include a power source, e.g., battery 11, and a driver 12 for converting the power source into energy suitable for powering up the light source 16, e.g., solid state light source. As noted above, the light 9 that is emitted from the light source 16 may be adjusted to correspond with a severity of changes in the medical condition of the user 15 of the wearable decorative alert device 10.

For example, although FIG. 4 illustrated a single light source 16, which may be provide by a single light emitting diode, embodiments have been contemplated in which the light source 16 is provided by a plurality of light emitting diode containing strings. In this example, the LEDS of each of the strings may be selected to provide different types of light that are addressable by a microcontroller 13. The microcontroller 13 can control the amount of current that is being passed through the individual strings of LEDs. This can provide that the light source 16 can be adjusted to emit light 9 having different colors, color temperatures and/or intensity. The microcontroller 13 may be in electrical communication with the transceiver 14 of the wearable decorative alert device 10. As noted above, the transreceiver 14 of the wearable decorative alert device 10 is in electrical communication with the transmitter 24 (e.g., transmitter to wearable device including light source 10) of the medical alert system 20. Therefore, command signals for changing the light 9 characteristics of the light source 16 for providing medical alert signatures can be received by the transceiver 14, and the changes effectuated through the microcontroller 13.

Referring to FIG. 4, a reflector may be employed to direct the light from the light source 16 through an optic. The optic may have the geometry of a gem to provide aesthetics of jewelry.

Referring back to FIG. 1, the method can continue with linking a monitoring device 35 to the medical alert system 20. The monitoring device 35 may be an internet of things (JOT) type device. In some embodiments, linking of the monitoring device 35 to the medical alert system 20 includes wireless communication between the monitoring device 35 and the medical alert system 20. As illustrated in FIG. 4, the medical alert system 20 includes a monitoring device receiver 22. This can be a transceiver for receiving an input data to the medical alert system 20.

The IOT devices 35a, 35b, 35c, 35d, 35e can be equipped with various types of sensors to collect information about themselves and their surroundings, and provide the collected information to the conference system 106 over the network 104.

In some embodiments, the monitoring devices 35 are internet of things (JOT) devices including at least one of an activity metrics of the user 35a, camera 35b, GPS 35c, a microphone 35d, health metrics sensor 35e of the user 15, or a combination thereof.

In some examples, the IOT devices 35a, 35b, 35c, 35d, 35e, or a hub that the IOT devices 35a, 35b, 35c, 35d, 35e, are in communication with include a cellular radio to establish a connection to the Internet via a cellular service such as a 4G (e.g., Mobile WiMAX, LTE) or 5G cellular data service. Alternatively, or in addition, the IOT devices or a hub that the IOT devices are in communication with include a may include a WiFi radio to establish a WiFi connection through a WiFi access point or router which couples the IOT devices 35a, 35b, 35c, 35d, 35e, or IOT hub to the Internet (e.g., via an Internet Service Provider providing Internet service to the end user), which in turn connect to the alert system 20/network 40. Of course, it should be noted that the underlying principles of the invention are not limited to any particular type of communication channel or protocol.

In one embodiment, the IoT devices 35a, 35b, 35c, 35d, 35e are ultra low-power devices capable of operating for extended periods of time on battery power (e.g., years). To conserve power, the local communication channels may be implemented using a low-power wireless communication technology such as Bluetooth Low Energy (LE). In this embodiment, each of the IoT devices 52a, 52b, 52c, 52d are equipped with Bluetooth LE radios and protocol stacks.

In one embodiment, the IoT platform includes an IoT app or Web application executed on user devices, e.g., the medical alert system 20, to allow users to access and configure the connected IoT devices 35a, 35b, 35c, 35d, 35e an IoT hub, and/or IoT service. The Web application may provide for communication over the network 40 to the alert system 60.

In one embodiment, the IoT devices may be a health metrics sensor 35e of the user 15, which can be a continuous glucose monitor (GCM). A continuous glucose monitor is a device used for monitoring blood glucose on a continual basis by people with either type I or type II diabetes. A continuous glucose monitor (CGM) takes a reading on set intervals with a small electrode placed under the skin and held in place by an adhesive. A transmitter attached to the electrode sends data to a separate receiver. It is noted that the CGM is only one example of a health metrics sensor 35e for the user 15. Other health metrics sensors 35a can measure heart rate, body temperature, oxygen level, and other like biometrics taken from the user 15.

In one embodiment, the IoT devices may be an activity metrics sensor 35a of the user 15. An activity metrics sensor 35a can measure from the user 15 the number of steps walked, heart rate, quality of sleep, steps climbed, and other personal metrics involved in fitness.

Another form of internet of things (IOT) sensor that is suitable for use as the connected IoT devices 35d to the medical alert system 20 through the network 40 includes a microphone 35d for measuring sounds, such as voices. The microphone 35d can record a user's speech. Recording a user's 15 speech can be helpful for analysis to determine if the user's speech is slurred, indistinct, or verbal skills generally decrease. This can be indicative of a diabetic having low blood sugar.

These IOT devices having a microphone 35d for measuring sounds may include virtual assistant type devices. A virtual assistant type device can receive questions by voice activation, and searches a database, or the internet, to provide an answer to the question.

Another form of internet of things (IOT) sensor that is suitable for use as the connected IoT devices 35b to the medical alert system 20 through the network 40 includes a video camera 35b for recording a user's actions and/or movements. In one example, if the user 15 is a diabetic, and the user's movements become erratic and/or his motion capabilities become diminished, video recordation of those actions can lead to analysis by the system that the diabetic user has low blood sugar, and the system may lead to the generation of a medical alert to be displayed by the wearable decorative alert device 10. Video information of the user 15 can also be used to determine if the user 15 is engaged in an activity/exercise/event that would impact measurements taken from Some examples of the IOT devices 35b that can include a video camera for include a personal computer, a computer monitor, a phone, a laptop, a tablet computer, a lightbulb, a luminaire, a lighting system, a door lock, a water heater, a sprinkler system, an air-conditioner, a thermostat, an alarm clock, a window shade, a switch, a smoke alarm, an electrical outlet, an alarm, a personal proximity sensor, a door sensor, a biometric sensor, a mobile device, an automotive sensor, a cooking device, an electrical breaker, a personal alert sensor, a motion sensor, a calendar, a television, a radio, a radio frequency identification (RFID) tag/RFID detector, a vehicle, an electric vehicle charger, a distributed generator (e.g. solar panel), a distributed energy storage (e.g. battery), a thermometer, and combinations thereof.

Another form of internet of things (TOT) sensor that is suitable for use as the connected IoT devices 35b to the medical alert system 20 through the network 40 includes a GPS 35c for recording a user's location. This can be helpful for locating locations that can be detrimental to a user's health.

Referring back to FIG. 1, the method may continue at block 4, which includes measuring health status of the user 15. The medical alert system 20 may continuously monitor a user's health status by getting continuous updates on the user 15 through measurements taken through the IOT devices 35a, 35b, 35c, 35d, 35e. This information can be used for comparison with the health baseline for the user from medical history that is provided in block 1 of this method for determining whether a change in a user's health status has occurred that would trigger a medical alert that is to be signaled through illumination of the light source 16 of the wearable decorative alert device 10. For example, the light source 16 for the wearable decorative alert device 10 may be LED lighting (or other mechanism for illumination and/or visual recognition) system embedded into a jewelry with communications capabilities. The jewelry get feeds from a cognitive engine, e.g., cognitive risk calculating engine 23, as depicted in FIG. 4, that is configured for an individual and captures information for other inputs that can be critical to determining the urgency.

More specifically, following receipt of data through the IOT devices 35a, 35b, 35c, 35d, 35e, the method may continue with determining with a cognitive risk evaluating engine 23 of the medical alert system 200 a level of medical alert provided by a setting of the light source 16 of wearable decorative alert device 10 that corresponds to the changes in the users 15 health status measured by the monitoring devices, i.e., IOT devices 35a, 35b, 35c, 35d, 35e at block 5 of FIG. 1.

In some embodiments, the step of determining with the alert system 20 if the content of the data through the IOT devices 35a, 35b, 35c, 35d, 35e, and the baseline determined from the medical records 30 and the medical care professional 25, warrants a high or low level of alert includes the cognitive risk evaluating engine 23 that employs at least one hardware device processor for performing a set of instruction stored on at least one memory device, in which the cognitive risk evaluating engine 23 analyzes the data from the monitoring devices and assigns weights to the data according to the baseline information for the health status of the user that was set at block 1 of the method depicted in FIG. 1. The cognitive risk evaluation engine 23 may be provided by a cognitive computing engine that can perform a machine learning technique, a natural language processing technique, and/or other big data techniques. In some embodiments, the cognitive risk evaluation engine 23 may utilize the cognitive computing to analyze the medical records 30, as well as the monitoring of the user 15 via the IOT devices 35a, 35b, 35c, 35d, 35e. For example, cognitive computing engine may analyze data regarding thousands of prior medically related scenarios from the users medical records 30 to train the cognitive risk evaluation engine 23 to recognize what aspects of a user's health or conduct being monitored by the IOT devices 35a, 35b, 35c, 35d, 35e warrants the issuance of a medical alert, and at what level of alert, e.g., high alert or low alert. After training the cognitive risk evaluation engine 23 can than employ cognitive computing to analyze the user's health status by getting continuous updates on the user 15 through measurements taken through the TOT devices 35a, 35b, 35c, 35d, 35e. For example, the cognitive risk evaluating engine 23 analyzes the data from the monitoring devices 35a, 35b, 35c, 35d, 35e and assigns weights to the data. Taking into account the data weighted in view of the baseline information, the cognitive risk evaluating engine 23 can compare the weighted inputs from all the different monitoring devices, and calculate whether the weighted inputs raise to a level of severity that would result in the issuance of a medical alert, as well as how high an alert should be issued.

Referring to FIG. 1, the method may further include illuminating the light source 16 at the level of the medical alert designed by the cognitive risk evaluating engine for signaling the changes in the users medical condition from the baseline of the user. The light source 16 may signal a medical alert by selecting certain light settings. For example, the light pattern of the light 9 being emitted by the light source 16 can be set to identify a high medical alert when the light pattern flickers at a high frequency, and can be set to a identify a lower medical alert when the light pattern flickers at a low frequency. In other examples, colors can be used to identify different levels of medical alert. For example, a high medical alert can be signed by the color red, and a low medical alert can be signed by the color yellow and/or green. In some embodiments, the system may further include a sensor on the jewelry that senses that the medical alert has been received and the user's 15 health condition is being handled, in which the sensor signals the medical alert system 20 to discontinue signaling and/or escalating the medical alert.

In some embodiments, the method links an IoT enabled piece of jewelry to an individual. The method may also link secondary IoT enabled systems to an individual, and determine risk level associated with change of data feeds. Thereafter, the method can modify lighting, or other visual cues, when risk levels change.

A system, method and apparatus is provided the meets the needs for medical attention based on IoT feeds and cognitive interpretation of individual historical needs. A method is also provided to identify the urgency of care needed for an individual based on different lighting patterns from jewelry.

In one example, a user 15 is a type-1 teenage diabetic. The user 15 does not want her continuous glucose monitor to beep when her blood sugar is starting to dip or the system determines that it may start to drop or an audio warning is not appropriate or workable. The user's 15 medical history 30 has shown that the user's motor and verbal skills start to decrease when the user's blood sugar goes below 45 mg/dl. In one example, the user's CGM starts predicting that her blood sugar will go to 60 mg/dl in the next 15 minutes and the wearable decorative alert device 10, e.g., jewelry starts, displaying a low yellow light indicating moderate risk. As no actions are taken, the system determines 30 minutes later that the user's 15 blood sugar is going to go to 40 mg/dl and the wearable decorative alert device 10 illuminates in a bright red light indicating high risk.

In another example, a different user 15 with medical history 30 may show no loss of skill until they have a blood sugar level of 70. In this example, this new user 15 would have their warning system take action when their blood sugar went below 80.

In another example, a user 15 has a heart condition and then user's 15 doctors 25 does not want the user's heart rate to go over 100. As the user's heart rate goes up to 90, as measured by the monitoring devices 35, and his smart watch, i.e., activity sensory 35a, indicates that the user's level of exercise is increasing. In response, the medical alert system 20 sends an illumination alert signal to the wearable decorative alert device 10, e.g., smartwatch, which starts blinking red. The red blinking signal indicates high risk.

In yet another example, a user 15 is a type-1 diabetic that is not wearing a continuous glucose monitor (CGM). Based on a change in his speech pattern and motion capabilities, the medial alert system 20 determines the user 15 is at risk and illuminates his wearable decorative alert device 10, e.g., tie clip, starts to blink yellow. The yellow blinking signal indicates moderate risk.

FIG. 3 is a block diagram illustrating a medical alert system 20. The medical alert system 20 may be used in combination with the method described in FIG. 1. Some elements of the medical alert system 20 have already been discussed in the description of FIG. 1. In one embodiment, the system for issuing medical alerts includes a registry 21 linking a wearable device 10 including a light source 16 for signaling medical alerts to a user medical history 36, wherein the medical history provides a baseline of the user 15. A monitoring device receiver 22 for receiving from a monitoring device 35a, 35b, 35c, 35d, 35e measurements of changes in a health status of a user 15 from the baseline of the user 15. In some embodiments, a cognitive risk evaluating engine 23 for setting a level of medical alert provided by a setting of the light source 10 corresponding to the changes in the users health status measured by the monitoring device. The system may further include a transmitter 24 for sending a signal to illuminate the light source at the level of the medical alert designated by the cognitive risk evaluating engine.

Figure 5:
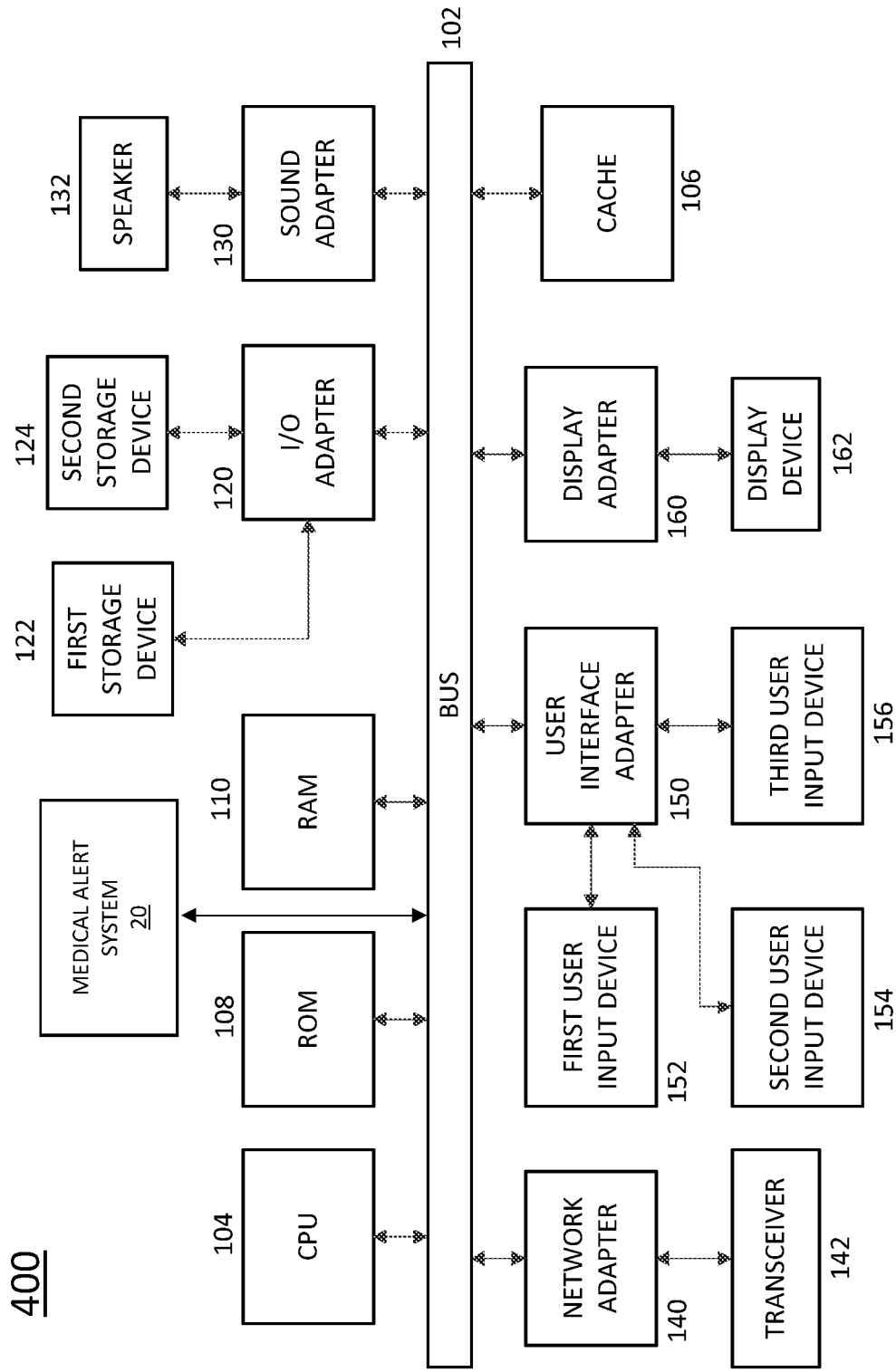
FIG. 5 is a block diagram illustrating a system that can incorporate the medical alert system depicted in FIG. 3, in accordance with one embodiment of the present disclosure.

The medical alert system 20 may be integrated into the processing system 400 depicted in FIG. 5. The processing system 400 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102. The bus 102 interconnects a plurality of components has will be described herein.

The system 400 depicted in FIG. 5, may further include a first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 400.

Of course, the processing system 400 may also include other elements (not shown), as readily contemplated by one of skill in the art, as well as omit certain elements. For example, various other input devices and/or output devices can be included in processing system 400, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 400 are readily contemplated by one of ordinary skill in the art given the teachings of the present invention provided herein.

The present invention may be a system, a method, and/or a computer program product at any possible technical detail level of integration. The computer program product may include a computer readable storage medium (or media) having computer readable program instructions thereon for causing a processor to carry out aspects of the present invention.

For example, the present disclosure provides a computer program product comprising a non-transitory computer readable storage medium having computer readable program code embodied therein for issuing medical alerts. The method actuated by the computer program product may include registering a user with a medical alert system, wherein said registering includes setting a medical history for a baseline of the user, and linking the system with a wearable device including a light source for signaling changes in the users medical condition from a baseline of the user; linking a monitoring device to the medical alert system; measuring changes in a health status of a user from the baseline of the user using the monitoring device; determining with a cognitive risk evaluating engine of the medical alert system a level of medical alert provided by a setting of the light source that corresponds to the changes in the users health status measured by the monitoring device; and illuminating the light source at the level of the medical alert designed by the cognitive risk evaluating engine for signaling the changes in the users medical condition from the baseline of the user.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The methods of the present disclosure may be practiced using a cloud computing environment. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 6:
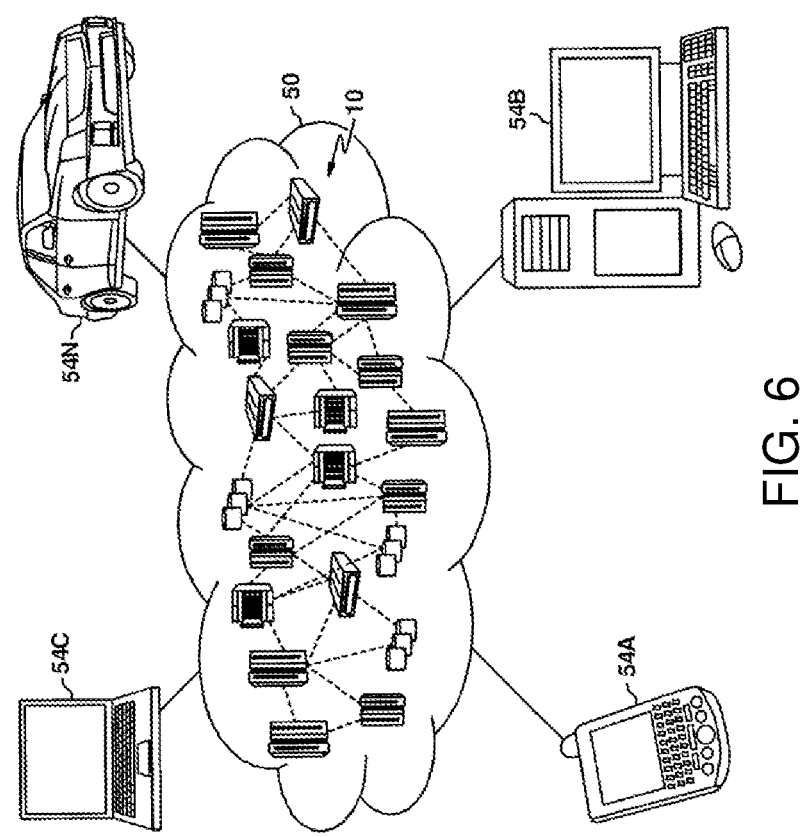
FIG. 6 depicts a cloud computing environment according to an embodiment of the present disclosure.

Referring now to FIG. 6, illustrative cloud computing environment 50 is depicted. As shown, cloud computing environment 50 includes one or more cloud computing nodes 51 with which local computing devices used by cloud consumers, such as, for example, mobile and/or wearable electronic devices 54A, desktop computer 54B, laptop computer 54C, and/or automobile computer system 54N may communicate. Nodes 110 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 51 and cloud computing environment 50 can communicate with any type of computerized device over any type of network and/or network addressable connection (e.g., using a web browser).

Figure 7:
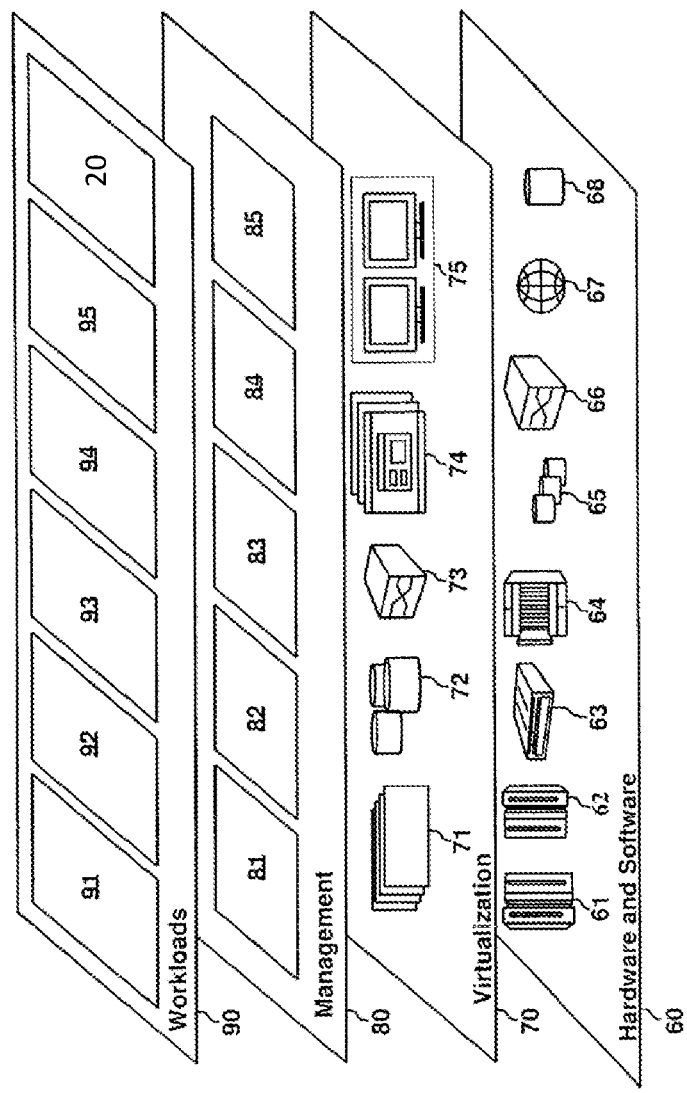
FIG. 7 depicts abstraction model layers according to an embodiment of the present disclosure.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below.

Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and medical alert system 20, which is described with reference to FIGS. 1-6.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of medical alert jewelry (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer implemented method for issuing medical alerts comprising:
   receiving permission from a user to register the user with a medical alert system, wherein said registering includes setting a medical history for a baseline of the user, and linking the system with a wearable device including a light source for signaling changes in the user's medical condition from a baseline of the user, wherein the baseline includes a blood sugar level, and severity levels for the user's medical condition above the baseline are set with increasing values calculated from changes in user conduct in speech clarity and physical motion above the blood sugar level;
   linking a monitoring device to the medical alert system, wherein the monitoring device is a continuous glucose monitor;
   measuring changes in a health status of a user from the baseline of the user using the monitoring device, the changes in health status including a health diagnostic measurement of a medical characteristic from the user in combination with a measurement of the user's conduct, the user's conduct being measured including speech clarity measured with a microphone and user movement measured from a video system;
   determining with a cognitive risk evaluating engine of the medical alert system a level of medical alert, the level of said medical alert determined by matching the severity level above the baseline to the changes in health states measured from the user, the level of medical alert designated by a setting of the light source that corresponds to the changes in the users health status measured by the monitoring device; and
   illuminating the light source at the level of the medical alert designed by the cognitive risk evaluating engine for signaling the changes in the users medical condition directed to a diabetic condition from the baseline of the user.

2. The computer implemented method of claim 1, wherein setting a medical history for a baseline of the user comprises registering medical records, medical care provider instructions or combinations thereof.

3. The computer implemented method of claim 1, wherein the wearable device including the light source for signaling changes in the users medical condition has a jewelry form factor selected from the group consisting of a ring, a necklace, a wrist band, an ankle band, a head band, earrings or a combination thereof.

4. The computer implemented method of claim 3, wherein the light source of the wearable device includes a form of solid state lighting.

5. The computer implemented method of claim 1, wherein the cognitive risk evaluating engine comprises a recurrent neural network.

6. The computer implemented method of claim 1, wherein the illuminating the light source at the level of the medical alert designed by the cognitive risk evaluating engine comprises a first light intensity setting for highest medical alert and a second light intensity setting for the lowest medical alert, the first light intensity being greater than the second light intensity.

7. A system for issuing medical alerts comprising:
   a registry linking a wearable device including a light source for signaling medical alerts to a user medical history, wherein the medical history provides a baseline of the user, wherein the baseline includes a blood sugar level, and severity levels for the user's medical condition above the baseline are set with increasing values calculated from changes in user conduct in speech clarity and physical motion above the blood sugar level;
   a monitoring device receiver for receiving from a monitoring device measurements of changes in a health status of a user from the baseline of the user, the monitoring device receiver receiving at least one health diagnostic measurement from the user and at least one user conduct measurement, the changes in health status including the health diagnostic measurement of a change in the medical characteristic from the user in combination with a correlated measurement of a change in the user's conduct, wherein the monitoring device is a continuous glucose monitor, and the user's conduct being measured including speech clarity measured with a microphone and user movement measured from a video system;
   a cognitive risk evaluating engine for setting a level of medical alert, the level of said medical alert determined by matching the severity level above the baseline to the changes in health states measured from the user, the level of medical alert designated by a setting of the light source corresponding to the changes in the user's health status measured by the monitoring device; and a transmitter for sending a signal to illuminate the light source at the level of the medical alert indicating a diabetic condition designated by the cognitive risk evaluating engine.

8. The system of claim 7, wherein setting a medical history for a baseline of the user comprises medical records, medical care provider instructions or combinations thereof.

9. The system of claim 7, wherein the wearable device has a jewelry form factor selected from the group consisting of a ring, a necklace, a wrist band, an ankle band, a head band, earrings or a combination thereof.

10. The system of claim 9, wherein the light source of the wearable device includes a form of solid state lighting.

11. The system of claim 9, wherein the cognitive risk evaluating engine comprises a recurrent neural network.

12. A computer program product comprising a computer readable storage medium having computer readable program code embodied therein for issuing medical alerts, the method comprising:

registering a user with a medical alert system, wherein said registering includes setting a medical history for a baseline of the user, and linking the system with a wearable device including a light source for signaling changes in the users medical condition from a baseline of the user, wherein the baseline includes a blood sugar level, and severity levels for the user's medical condition above the baseline are set with increasing values calculated from changes in user conduct in speech clarity and physical motion above the blood sugar level;

linking a monitoring device to the medical alert system, wherein the monitoring device is a continuous glucose monitor, and the user's conduct being measured including speech clarity measured with a microphone and user movement measured from a video system;

measuring changes in a health status of a user from the baseline of the user using the monitoring device, the changes in health status including a health diagnostic measurement of a medical characteristic from the user in combination with a measurement of the user's conduct, the user's conduct being measured including speech clarity measured with a microphone;

determining with a cognitive risk evaluating engine of the medical alert system a level of medical alert, the level of said medical alert determined by matching the severity level above the baseline to the changes in health states measured from the user, the level of medical alert designated by a setting of the light source that corresponds to the changes in the users health status measured by the monitoring device; and illuminating the light source at the level of the medical alert designed by the cognitive risk evaluating engine for signaling the changes in the users medical condition indicating a diabetic condition from the baseline of the user.

13. The computer program product of claim 12, wherein setting a medical history for a baseline of the user comprises registering medical records, medical care provider instructions or combinations thereof.

* * * * *